US009399079B2

(12) United States Patent
McMinn et al.

(10) Patent No.: US 9,399,079 B2
(45) Date of Patent: Jul. 26, 2016

(54) MODULAR MULTIFUNCTION FRAGRANCE EMITTER

(71) Applicant: Home & Garden Party, Ltd., Marshall, TX (US)

(72) Inventors: David W. McMinn, Marshall, TX (US); Steve Carlile, Marshall, TX (US); Lowell W. Newman, Hallsville, TX (US)

(*) Notice: Subject to any disclaimer, the term of this patent is extended or adjusted under 35 U.S.C. 154(b) by 54 days.

(21) Appl. No.: 14/298,650

(22) Filed: Jun. 6, 2014

(65) Prior Publication Data

US 2015/0017071 A1    Jan. 15, 2015

Related U.S. Application Data

(63) Continuation-in-part of application No. 13/934,202, filed on Jul. 2, 2013.

(51) Int. Cl.
| | |
|---|---|
| *F24F 3/14* | (2006.01) |
| *A61M 16/00* | (2006.01) |
| *A61L 9/03* | (2006.01) |
| *C11C 5/00* | (2006.01) |

(52) U.S. Cl.
CPC . *A61L 9/03* (2013.01); *A61L 9/032* (2013.01); *C11C 5/002* (2013.01); *A61L 2209/12* (2013.01); *A61L 2209/135* (2013.01); *Y10T 29/49826* (2015.01)

(58) Field of Classification Search
None
See application file for complete search history.

(56) References Cited

U.S. PATENT DOCUMENTS

| | | | |
|---|---|---|---|
| D245,705 | S | 9/1977 | Fukada |
| D288,842 | S | 3/1987 | Kwiatkowski |
| D289,678 | S | 5/1987 | Kwiatkowski |
| D320,266 | S | 9/1991 | Kunze |
| D338,522 | S | 8/1993 | Muderlak |
| D348,312 | S | 6/1994 | Schwartz et al. |
| 5,891,400 | A | 4/1999 | Ansari et al. |
| 6,236,807 | B1 | 5/2001 | Ruffolo et al. |
| 6,390,453 | B1 | 5/2002 | Frederickson et al. |
| 6,511,531 | B1 | 1/2003 | Cartellone |
| 6,556,272 | B1 | 4/2003 | Du et al. |
| D521,621 | S | 5/2006 | Slater |
| 7,154,579 | B2 | 12/2006 | Selander et al. |
| D544,084 | S | 6/2007 | Michaels et al. |
| D553,729 | S | 10/2007 | Bayly |
| D612,473 | S | 3/2010 | Valentino et al. |
| D633,190 | S | 2/2011 | Abbondanzio et al. |
| D641,858 | S | 7/2011 | Thompson |
| D651,301 | S | 12/2011 | Albee et al. |
| 2002/0068010 | A1 | 6/2002 | Laudamiel-Pellet et al. |
| 2003/0007887 | A1 | 1/2003 | Roumpos et al. |
| 2003/0097936 | A1 | 5/2003 | Maleeny et al. |

(Continued)

OTHER PUBLICATIONS

International Search Report for Co-Pending PCT Application No. PCT/US2015/028473 mailed Jul. 22, 2015, 2 pgs.

(Continued)

*Primary Examiner* — Thor Campbell
(74) *Attorney, Agent, or Firm* — Gardere Wynne Sewell L.L.P.

(57) ABSTRACT

An apparatus for producing a fragrance includes a heating element, a barrier that at least partially surrounds the heating element and a shell that at least partially surrounds the barrier. At least a portion of the volume between the barrier and the shell is configured to hold one or more solid fragrance carriers. A heat induced airflow through the apparatus causes the solid fragrance carriers to emit a fragrance.

17 Claims, 8 Drawing Sheets

(56) References Cited

U.S. PATENT DOCUMENTS

| | | |
|---|---|---|
| 2003/0168751 A1 | 9/2003 | Bartsch et al. |
| 2005/0074358 A1 | 4/2005 | Hart et al. |
| 2005/0094988 A1 | 5/2005 | Yip et al. |
| 2005/0147523 A1 | 7/2005 | Laudamiel-Pellet et al. |
| 2005/0169813 A1 | 8/2005 | D'Amico et al. |
| 2005/0285538 A1 | 12/2005 | Jaworski et al. |
| 2008/0318177 A1 | 12/2008 | Requejo et al. |
| 2009/0004614 A1 | 1/2009 | Furner et al. |
| 2009/0148342 A1 | 6/2009 | Bromberg et al. |
| 2010/0021855 A1 | 1/2010 | Requejo et al. |
| 2010/0059601 A1 | 3/2010 | Bankers et al. |
| 2010/0178042 A1 | 7/2010 | Neumann et al. |
| 2010/0269826 A1 | 10/2010 | Colombo et al. |
| 2011/0049259 A1 | 3/2011 | Beland et al. |
| 2011/0253798 A1 | 10/2011 | Tucker et al. |
| 2011/0286726 A1 | 11/2011 | Baraky |
| 2012/0024975 A1 | 2/2012 | Sharma et al. |
| 2012/0199665 A1 | 8/2012 | Neumann |
| 2014/0377130 A1 | 12/2014 | Edwards et al. |
| 2015/0010293 A1 | 1/2015 | Newman |
| 2015/0017071 A1 | 1/2015 | McMinn et al. |

OTHER PUBLICATIONS

Written Opinion for Co-Pending PCT Application No. PCT/US2015/028473 mailed Jul. 22, 2015, 6 pgs.

International Search Report for PCT Application No. PCT/US2014/041377 Issued Sep. 9, 2014, 4 pgs.

Written Opinion for PCT Application No. PCT/US2014/041377 Issued Sep. 9, 2014, 5 pgs.

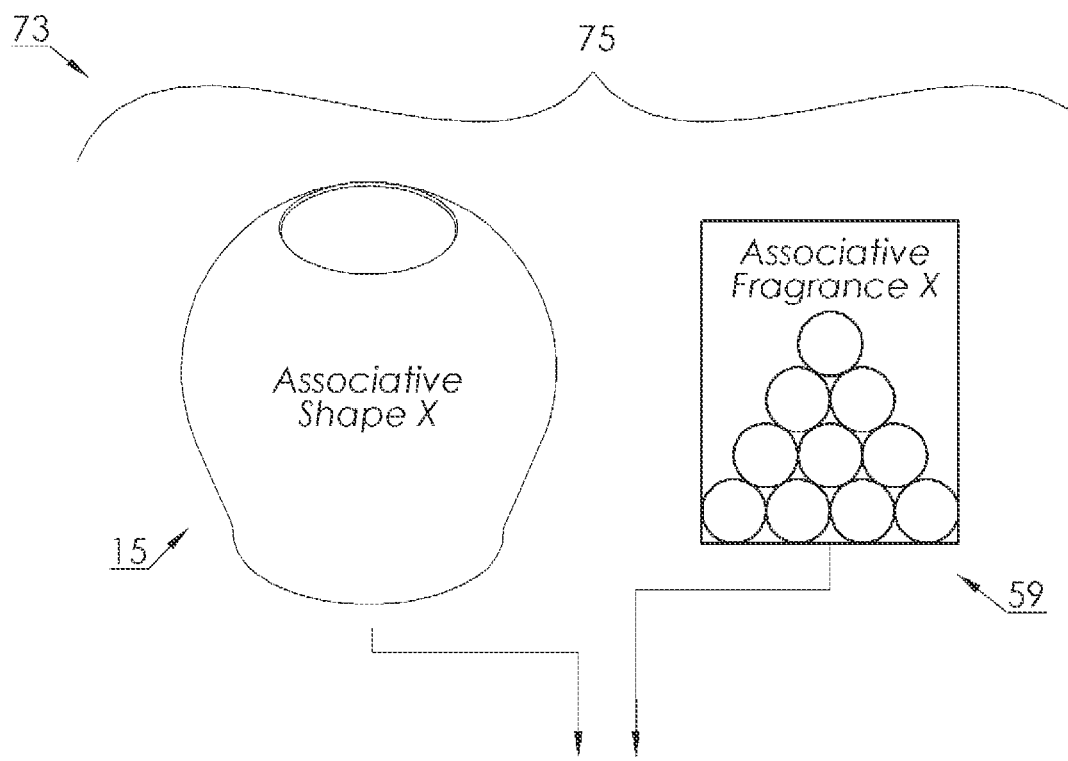
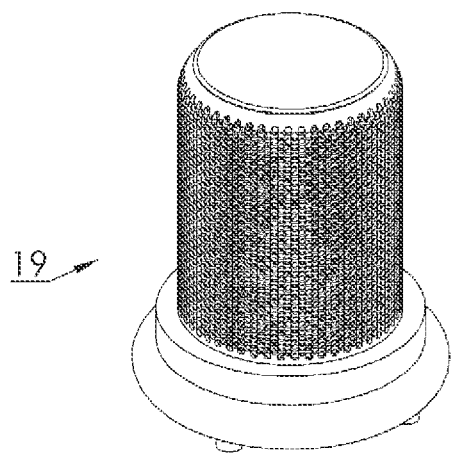
Fig. 5

MODULAR MULTIFUNCTION FRAGRANCE EMITTER

CROSS-REFERENCE TO RELATED APPLICATIONS

This application is a continuation-in-part patent application of U.S. patent application Ser. No. 13/934,202 filed Jul. 2, 2013 and entitled "Modular Multifunction Fragrance Emitter," which is incorporated here by reference in its entirety.

TECHNICAL FIELD

This disclosure relates to fragrance emitters and, more particularly, to fragrance emitters for solid fragrance carriers.

BACKGROUND OF THE DISCLOSURE

Fragrance emitters are commonly configured to receive and evaporate fragrance from liquid and/or liquefiable fragrance carriers such as fragrance-infused water, oil or wax. Such fragrance emitters provide fragrance to the surrounding area in various ways. For example, some emitters utilize a wick to carry a liquid fragrance carrier into a ventilation shaft through which ambient air is forced by a fan. The use of a wick for fragrance carrier transport in conjunction with forced aeration may allow for controlled and interruptible scent emission. Nevertheless, the wick requires delicate handling, occasional replacement, and does not allow for much customization.

SUMMARY

A modular fragrance emitter for solid fragrance carriers has a base that includes a heating element and a shell disposed on the base that includes a fragrance dispensing opening. The shell rests on the base and may be held in position by a permeable screen that extends upward surrounding the heating element. A fragrance carrier cavity is defined between the permeable screen and the shell. The fragrance carrier cavity is preferably filled with solid fragrance carriers. A ventilation channel is open to ambient air at its bottom end and terminates at a fragrance dispense opening that is preferably at the top of the shell. The permeable screen is placed at some point across the ventilation channel such that the ambient air that has entered the ventilation channel has to pass through the permeable screen before the air continues through the fragrance carrier cavity.

Since the permeable screen is positioned around the heating element, the permeable screen may be irradiatively heated by the heating element. The permeable screen may pass its heat to the air to provide a simple and safe heat transfer that allows the heating element to heat the fragrance carriers. At the same time, the large contact area of the permeable screen provides for an efficient and balanced heat transfer to the air. This may provide for balanced warming of the solid fragrance carriers and may provide for design freedom of the fragrance carrier cavity to accommodate fragrance carriers of various sizes, shapes and compositions. The design freedom of the fragrance carrier cavity may also allow for various shapes of shells that may be combined with various bases. Different shell shapes may be associated with various themes, characters or consumer goods and may be employed for specific occasions and applications.

The shell and permeable screen may further be light permeable. In embodiments in which the heating element produces light, the light from the heating element may pass through the permeable screen and illuminate the solid fragrance carriers. In some embodiments, light from the solid fragrance carriers may shine through the shell. This effect may be employed for decorative purposes and/or to visually convey the scent composition of the fragrance carriers, as the fragrance carriers may be color coded to indicate their fragrance.

The solid fragrance carriers may be color coded to allow for a user to visually identify and combine various carrier scents. Custom scents may be composed by counting and combining various fragrance carriers of different colors, shapes or sizes. The combined composition of fragrance carriers may be visually verified when the fragrance carriers are in an illuminated condition. In some embodiments, the solid fragrance carriers may be associated with a shaped shell. For example, in one embodiment, the shell may resemble a Christmas tree and the solid fragrance carriers may contain fir fragrance.

In another aspect, there is described an apparatus for producing a fragrance that include a heating element, a barrier that at least partially surrounds the heating element, and a shell that at least partially surrounds the barrier. At least a portion of a volume between the barrier and the shell may be configured to hold a fragrance carrier that is heated by the heating element to produce a fragrance.

In certain embodiments, the apparatus includes a base that is coupled to the heating element and that supports the barrier and the shell.

In other embodiments, the base includes one or more feet that hold at least a portion of the base above a surface on which the feet are resting to allow air to enter the apparatus through the base.

In another embodiment, the base includes an opening to allow ambient air to enter the apparatus. The apparatus may include a ventilation channel that extends between the opening and a fragrance dispensing opening in the shell.

In yet another embodiment, the opening is positioned in the base at a location between the heating element and the barrier.

In still another embodiment, the opening is positioned in the base at a location between the barrier and the shell.

In some embodiments, there are two or more openings and at least one of the openings is located in the base between the heating element and the barrier and another opening is located in the base between the barrier and the shell.

In another embodiment, the base includes a plurality of openings positioned around a perimeter of the heating element to allow ambient air to pass through the base and into an area between the heating element and the barrier.

In certain embodiments, the shell includes a first opening positioned adjacent to the heating element and an opposite, second opening that is larger than the first opening.

In other embodiments, the barrier includes an air permeable material and the shell includes an air impermeable material.

In another embodiment, the barrier includes an air impermeable material and the shell includes an air permeable material.

In certain embodiments, the barrier and the shell include an air permeable material.

In other embodiments, the barrier and the shell include an air impermeable material.

In another aspect, there is described an apparatus for producing a fragrance that includes a base, a first barrier, a second barrier and a cavity. The base may include a heating element. The first barrier at least partially surrounds the heating element and the second barrier at least partially surrounds the first barrier. The cavity is located between the first barrier and the second barrier to hold a fragrance carrier.

In certain embodiments, the first and second barriers are light permeable.

In other embodiments, the first barrier includes a receptacle for a liquid or liquefiable fragrance carrier.

In a further aspect, there is described an apparatus for producing a fragrance that includes a base, a first barrier, a second barrier, and a fragrance cavity. The base includes an air opening. The fragrance cavity is configured to hold one or more fragrance carriers and is located between the first barrier and the second barrier. In some embodiments, air from the air passage may pass through the first barrier and into the fragrance cavity.

In certain embodiments, the first and second barriers contact the base and the air opening is located in the base between the first barrier and the second barrier.

In other embodiments, the air opening is located in the base and is surrounded by the first barrier.

In another embodiment, the base includes an upper wall, a side wall and an air cavity between the upper wall and the side wall. The apparatus may include a ventilation channel that extends from the air cavity, through the air opening and into the fragrance cavity.

In another aspect, there is described a method for manufacturing a fragrance emitter. The method includes providing a screen, a shell and a base that includes an air inlet. The shell includes a fragrance dispensing opening to release fragrance into ambient air. The method includes positioning the shell at least partially around the screen and positioning the screen and the shell on the base to form a ventilation channel extending between the air inlet and the fragrance dispensing opening. A space between the screen and the shell makes up a fragrance carrier cavity.

In some embodiments, the method includes placing one or more solid fragrance carriers in the fragrance carrier cavity.

In other embodiments, the method includes coupling a heating element to the base.

In still other embodiments, the method includes positioning a fan in the base to produce an airflow.

Other aspects, features, and advantages will become apparent from the following detailed description when taken in conjunction with the accompanying drawings, which are a part of this disclosure and which illustrate, by way of example, principles of the inventions disclosed.

DESCRIPTION OF THE FIGURES

The accompanying drawings facilitate an understanding of the various embodiments.

FIG. 5 is a schematic view of another embodiment of a modular fragrance system in accordance with this disclosure.

DETAILED DESCRIPTION

Figure 1:
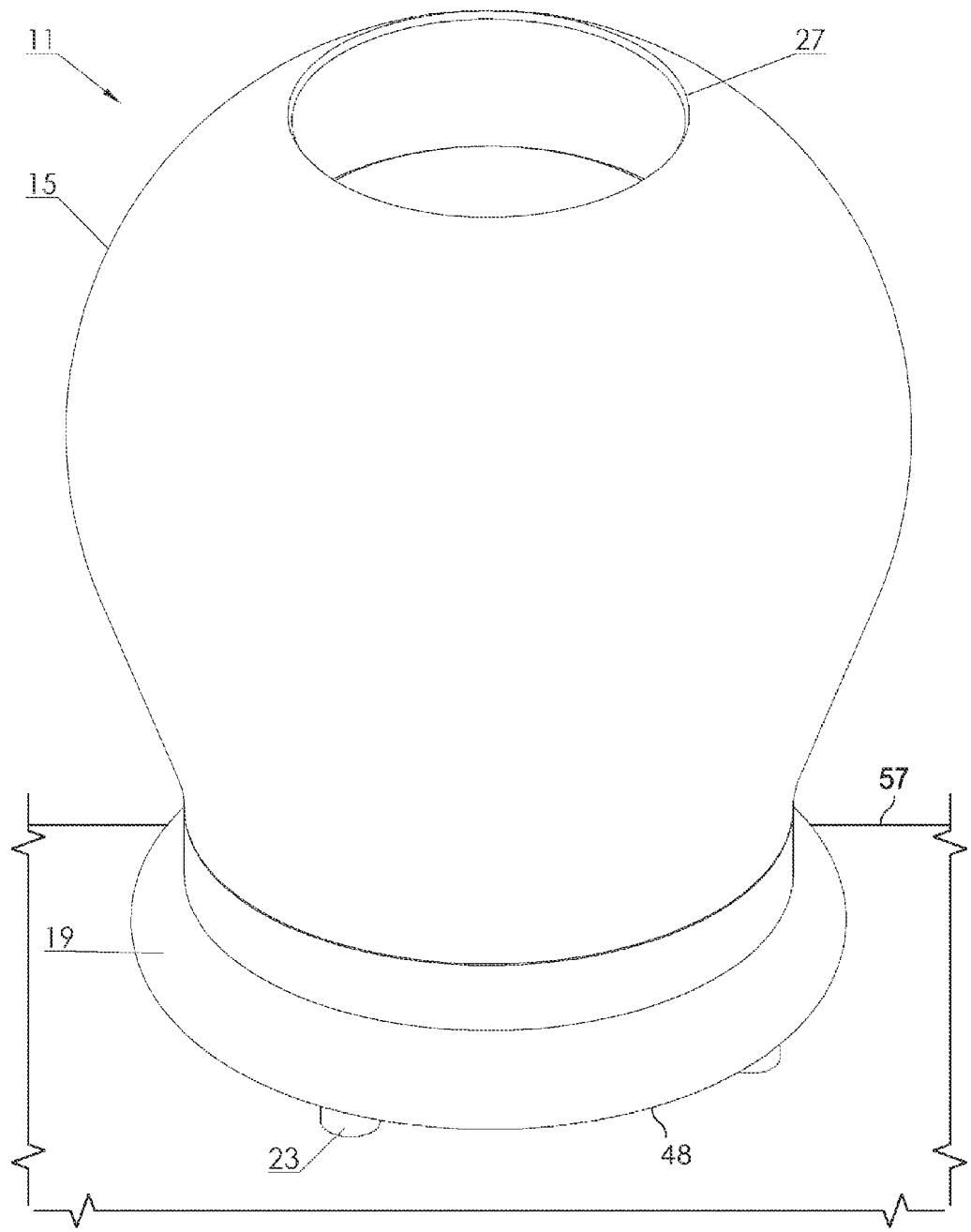
FIG. 1 is a perspective view of an embodiment of a fragrance emitter in accordance with this disclosure.

FIG. 1 is a perspective view of an embodiment of a fragrance emitter 11 that includes a base 19 and a shell 15 that rests on the base 19. The shell 15 has a fragrance dispense opening 27 disposed in an upper part of the shell 15 that is configured to allow air to flow into and out of the fragrance emitter 11, as will be described in more detail below. The shell 15 and the fragrance dispensing opening 27 may be any suitable shape and size. The shell 15 rests on the base 19 and may be removable from the base 19 or may be permanently coupled to the base 19 in any suitable manner, such as, for example, by an adhesive or one or more mechanical fasteners.

The base 19 may include feet 23 that extend from a bottom surface 48 of the base 19 and keep the base 19 in a spaced apart relationship with a surface 57 upon which the base 19 is placed. As described in more detail below, ambient air may pass between the base 19 and the surface 57 upon which the base 19 is placed, through the base 19 and then through the fragrance dispensing opening 27 to dispense a fragrance into the ambient air. By allowing ambient air to enter the modular fragrance emitter 11 below the base 19 and exit at the fragrance dispensing opening 27 at or near the top of the emitter 11, an unassisted, thermally-induced air flow through the modular fragrance emitter 11 is provided when a heating element 55 (FIG. 3) is engaged. In addition, the concentric alignment of the fragrance dispensing opening 27 and the base 19 allows for a balanced aeration of the fragrance carriers 59 (FIG. 3) located within the modular fragrance emitter 11.

Figure 2:
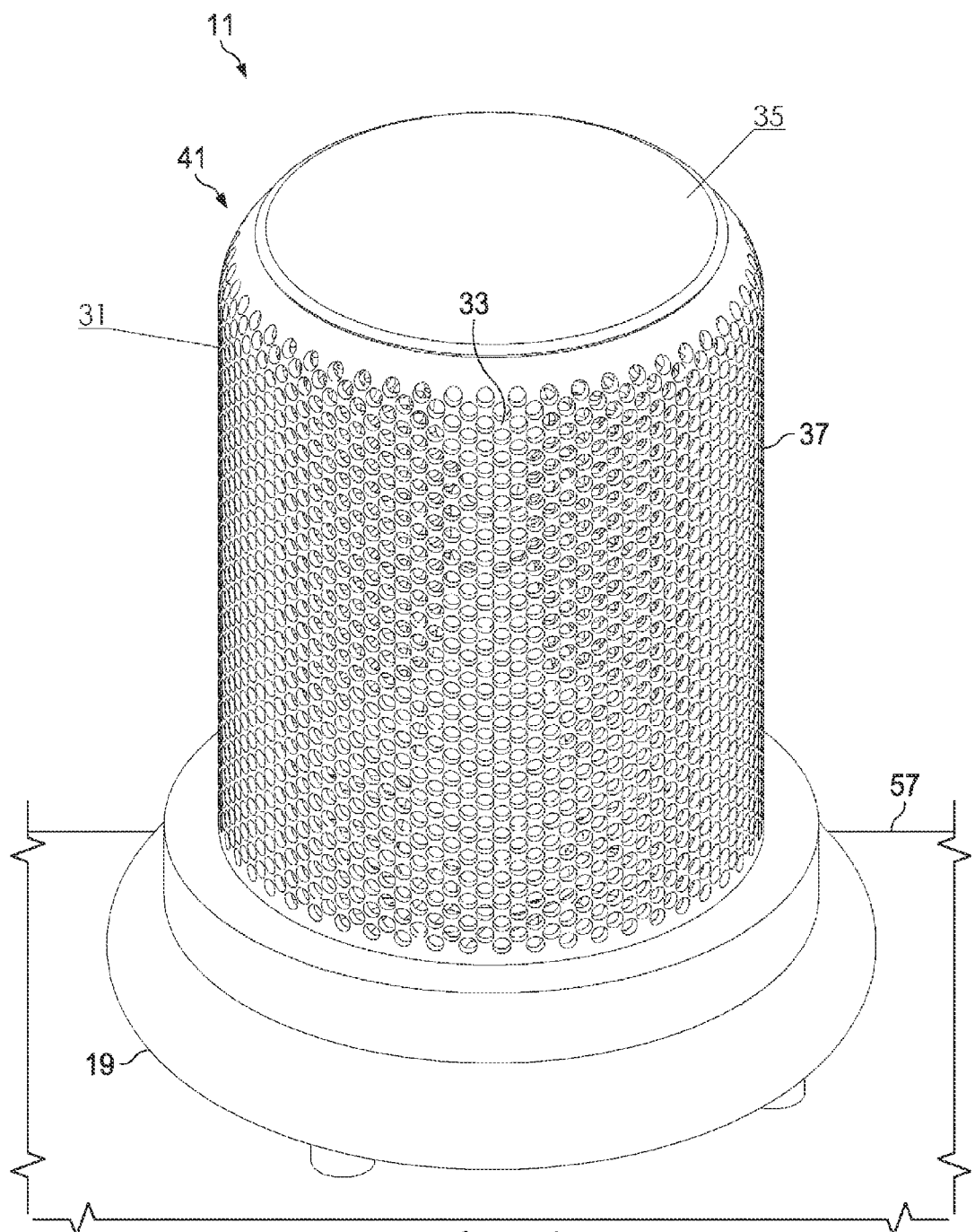
FIG. 2 is a perspective view of the fragrance emitter of FIG. 1 with the shell removed.

FIG. 2 is a perspective view of the modular fragrance emitter 11 of FIG. 1 with the shell 15 removed so that the permeable screen 31 is visible. The permeable screen 31 rests on the base 19 and may be removable from the base 19 or may be permanently coupled to the base 19. In some embodiments, the permeable screen 31 and the shell 15 are placed in a corresponding groove (not shown) on the base 19 to hold the permeable screen 31 and the shell 15 in place with respect to the base 19. The permeable screen 31 is located adjacent to the heating element 55 (FIG. 3) and, in some embodiments, surrounds the heating element 55 so that the permeable screen 31 is irradiativly heated by the heating element 55. The permeable screen 31 includes an air permeable surface 33 that allows air to pass therethrough and may also include an air impermeable surface 35 that does not allow air to pass therethrough, such as, for example, the cup-shaped impermeable surface 35 in the embodiment of FIG. 2. The permeable surface 33 may be permeable to air so that heated air from the heating element 55 (FIG. 3) that has passed by the fragrance carriers 59 (FIG. 3) can travel through the permeable surface 33 and out of the fragrance dispensing opening 27. The permeable surface 33 may cover the entire permeable screen 31 or may cover only part of the permeable screen 31. In some embodiments, for example, the permeable screen 31 includes a permeable surface 33 on a lateral surface 37 of the permeable screen 31 and an impermeable surface 35 in the shape of a cup on an upper end 41 of the permeable screen 31, as shown in FIG. 2.

The impermeable surface 35 of the permeable screen 31 may be configured in the shape of a cup or chalice for containing a liquid or liquefiable fragrance carrier 71 (FIG. 4), such as one or more wax cubes, water or oil based fragrance solutions, or other liquefiable fragrance products. The impermeable surface 35 is preferably removably positioned above the heating element 55 (FIG. 3) at the upper end 41 of the permeable screen 31 such that heated air from the heating element 55 passes under, around and over the impermeable surface 35. In some embodiments, the impermeable surface (s) 33 of the permeable screen 31 are permanently coupled to the remainder of the permeable screen 31 and in other embodiments the impermeable surface(s) 33 are separable from the remainder of the permeable screen 31.

Figure 3:
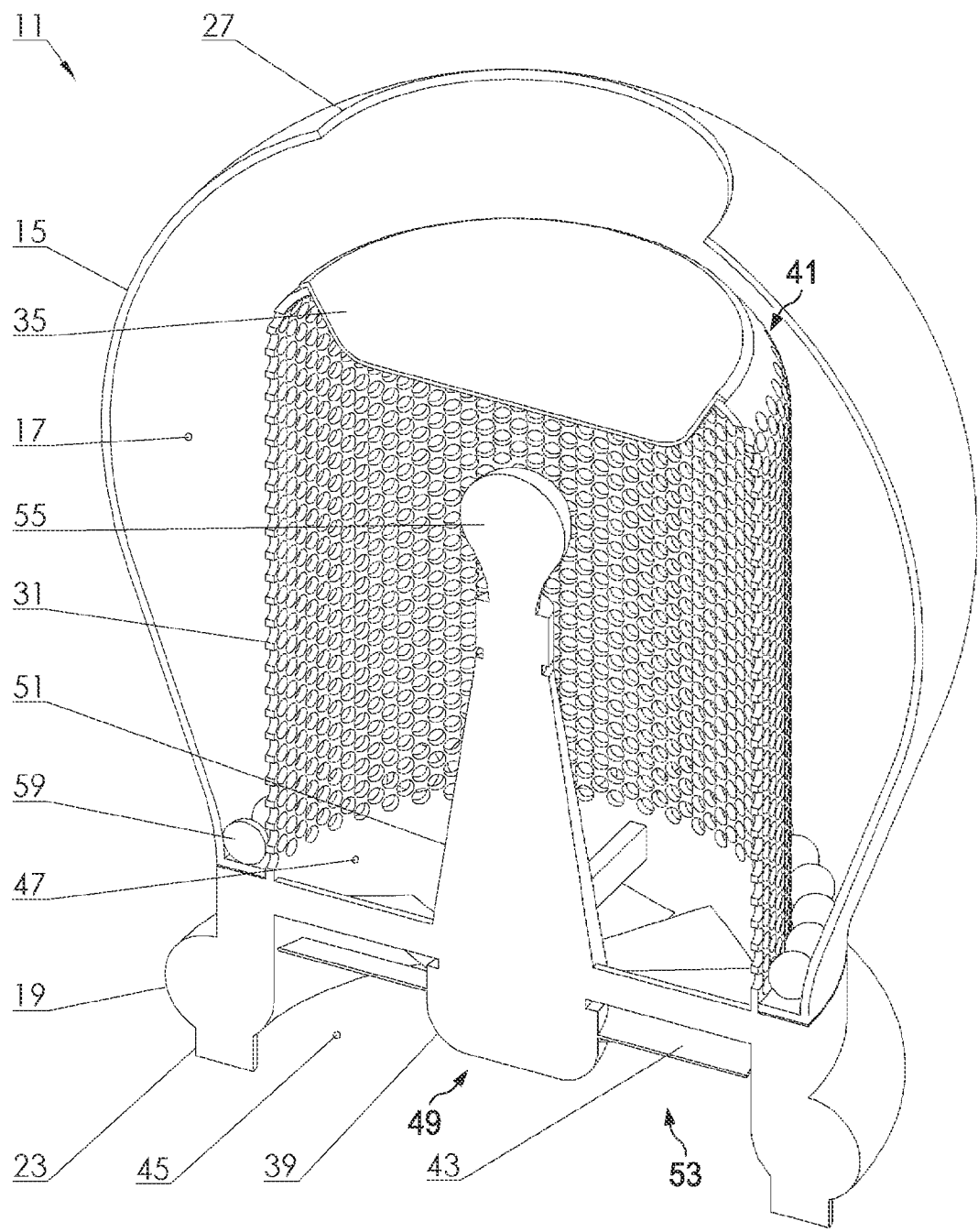
FIG. 3 is a cutaway perspective view of the fragrance emitter of FIG. 1 cut along a vertical plane.

FIG. 3 is the perspective view of the modular fragrance emitter 11 of FIG. 1 cut along a vertical plane so that the permeable screen 31, the heating element 55, a base core 51, a fan 49, the base 19 and the feet 23 are shown. The permeable screen 31 at least partially surrounds the heating element 55 and provides a barrier between the heating element 55 and a fragrance carrier cavity 17, as will be described in more detail below. The heating element 55 may be positioned on a base core 51 to elevate the heating element 55 above the base 19. In other embodiments, such as the embodiment shown in FIG. 7, the heating element 118 is more closely positioned to the base 106. In other embodiments, the heating element 55 may be positioned at any suitable distance from the base 19 or directly on the base 19. The heating element 55 may be any suitable heating device, such as, for example, a light bulb, candle, burner, metal heating element or other heat producing device. In some embodiments, the modular fragrance emitter 11 may include more than one heating element 55 and each heating element 55 may be of the same type or each heating element 55 may be of a different type. In some embodiments, the heating element 55 produces light when engaged. In some embodiments, the amount of heat and/or light produced by the heating element 55 is adjustable.

In the embodiment of FIG. 3, the base 19 includes a fan 49 to force air through the base 19, through the permeable screen 31, into the fragrance carrier cavity 17 and out of the fragrance dispensing opening 27. The fan 49 includes a fan motor 39 and fan blades 43 positioned in the base 19. In some embodiments, a user engages the fan 49 to dispense fragrance from the fragrance emitter 11 and the user disengages the fan 49 to reduce or eliminate fragrance emission from the fragrance emitter 11.

The modular fragrance emitter 11 may also have a ventilation channel 47 that passes through the modular fragrance emitter 11. The ventilation channel 47 starts at an air inlet 45 at or near the opening 53 in the base 19. The ventilation channel 47 extends around the base core 51 and heating element 55 and through the permeable screen 31. The ventilation channel 47 terminates at the fragrance dispensing opening 27. The ventilation channel 47 passes through the permeable screen 31 such that ambient air in the ventilation channel 47 is heated by the permeable screen 31. The permeable screen 31 may be made of a thermally conductive material, such as aluminum, so that heat is distributed through the entire permeable screen 31, and so that, in some embodiments, the entire permeable screen 31 remains at substantially the same temperature. Because of this, and due to a homogeneous air permeability of the permeable screen 31, the ambient air passing along the ventilation channel 47 and through the permeable screen 31 may be substantially evenly heated. At the same time, the permeable screen 31 may provide a large cross section area with balanced air flow restriction such that air passes through the permeable screen 31 with substantially equal speed. The equal air flow speed and air temperature may provide for an even heating and fragrance gassing of the fragrance carriers 59 that are contained in a fragrance carrier cavity 17.

The fragrance carrier cavity 17 is located between the shell 15 and the permeable screen 31 and receives fragrance carriers 59 through the fragrance dispense opening 27. For the purpose of clarity in FIG. 3, only a few fragrance carriers 59 are depicted at the bottom of the fragrance carrier cavity 17; however, the entire carrier cavity 17 may be filled. The permeable screen 31 is a boundary of the fragrance carrier cavity 17 such that the solid fragrance carriers 59 are at least partially contained via the permeable screen 31 and such that the ambient air immerses the fragrance carriers 59 after passing through and being heated by the permeable screen 31 and/or the heating element 55. The outer boundary of the fragrance carrier cavity 17 is the shell 15.

The ventilation channel 47 has a generally vertical orientation such that a natural thermally induced air flow may occur while the heating element 55 is actuated. Due to the air flow restriction of the permeable screen 31, and in the absence of any thermally induced buoyant air flow, the solid fragrance carriers 59 may remain substantially free of aeration when the heating element 55 is not actuated. Thus, fragrance release may be controlled by turning on and off the heating element 55. Thermally induced air flow may be further assisted by the fan 49 due to the location of the fan in the ventilation channel 47. The fan 49 may be mounted at the bottom of a base core 51 so that it is held at the center of the ventilation channel 47.

As discussed above, in some embodiments the permeable screen 31 includes an air impermeable surface 35 in a shape that retains a liquefiable fragrance carrier 71 (FIG. 4), a liquid fragrance carrier (not shown) or any other type of fragrance carrier. Aeration of the liquefiable fragrance carrier 71 located in the impermeable surface 35 is substantially reduced without air flow through the ventilation channel 47. As such, fragrance release from the liquefiable fragrance carrier 71 is controlled by controlling the air flow through the ventilation channel 47.

The base 19, the screen 31 and the shell 15 may be removably coupled together to provide a modular configuration of the fragrance emitter 11. This may provide for design freedom, for example, by combining shells 19 of different shapes with bases 19 of different shapes to create an overall theme, character and/or consumer good associative product.

The permeable screen 31 and the shell 15 may be at least partially light permeable. As such, in those embodiments in which the heating element 55 emits light, the light emitted by the heating element 55 may at least partially illuminate the solid fragrance carriers 59 through the permeable screen 31 and the illuminated solid fragrance carriers 59 may be at least partially visible through the shell 15. The permeable screen 31 and the shell 15 may also include colored surfaces that are illuminated by the light emitted by the heating element 55.

Figure 4:
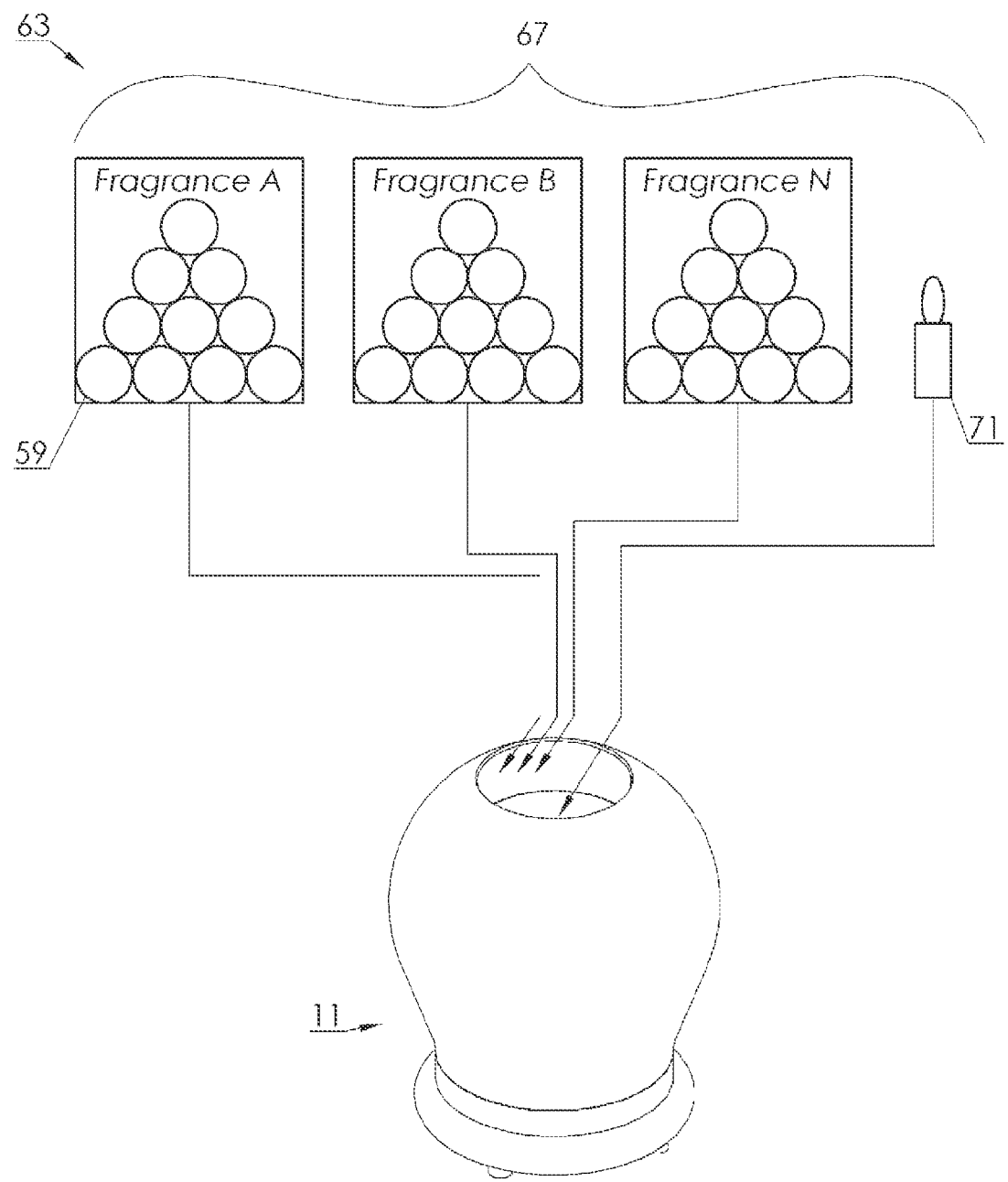
FIG. 4 is a schematic view of an embodiment of a modular fragrance system in accordance with this disclosure.

Referring to FIG. 4, a customizable scent emitting system 63 is shown which includes a modular fragrance emitter 11 and base fragrance carriers 67. The base fragrance carriers 67 may include solid fragrance carriers 59 and liquefiable fragrance carriers 71. Any other suitable fragrance carrier may also be included in the base fragrance carriers 67. The base fragrance carriers 67 may be combined and customized as they are applied to the modular fragrance emitter 11. The solid fragrance carriers 59 may be color coded in accordance with their fragrance such that when the solid fragrance carriers 59 are illuminated by the heating element 55, the illumination is customized and is a visual indication of the solid fragrance carriers 59 or mixture of solid fragrance carriers 59 inside the modular fragrance emitter 11. In this system 63, shells 15 that are associated with different themes, characters and/or consumer goods may be combined with various scents to further customize the modular fragrance emitter 11.

Referring to FIG. 5, a combined object and related scent advertising system 73 may feature a base 19 with a solid fragrance carrier direct heating and aeration configuration described above and an associative shape/scent set 75 including a shell 15 having an associative theme, character and/or consumer good shape and including the solid fragrance carriers 59 having an associative fragrance related to the selected associative shell 15 shape. For example, the shell 15 may be shaped like a head of a well-known comic book superhero and the associative fragrance may be selected to be associated with the effect of his particular superpower. In another example, the shell 15 may be shaped like a well-known chocolate product and the associative fragrance may be selected to be associated with that chocolate product.

Referring again to FIG. 3, to operate the modular fragrance emitter 11, and/or the systems 63 (FIG. 4) or 73 (FIG. 5), a selected shell 15 may be placed on the base 19 over the permeable screen 31 thereby establishing the fragrance carrier cavity 17 for solid fragrance carriers 59 and establishing the ventilation channel 47. This may be done at a factory site and/or at an end user site. A selected fragrance carrier 59 or mixture of fragrance carriers 59 may then be placed into the fragrance carrier cavity 17, for example, through the fragrance dispensing opening 27. Optionally, a liquefiable fragrance carrier 71 (FIG. 4) may be placed in the cup-shaped impermeable surface 35. The heating element 55 may be actuated by connecting it to an electricity source (not shown), which will start aeration and heating of the fragrance carriers 59, 71. Optionally, the fan 49 may also be actuated together with the heating element 55. As air flows past the fragrance carriers 59, 71, fragrance evaporates and is emitted through the fragrance dispensing opening 27. To stop or reduce fragrance emission, the fan 49 and heating element 55 may be disengaged. While the heating element 55 and the fan 49 are turned off, the heating and aeration of the fragrance carriers 59, 71 may be reduced or eliminated. In some embodiments, the fragrance emission of the modular fragrance emitter 11 is not completely eliminated when the heating element 55 and the fan 49 are turned off but rather the emission rate is simply reduced.

Figure 6:
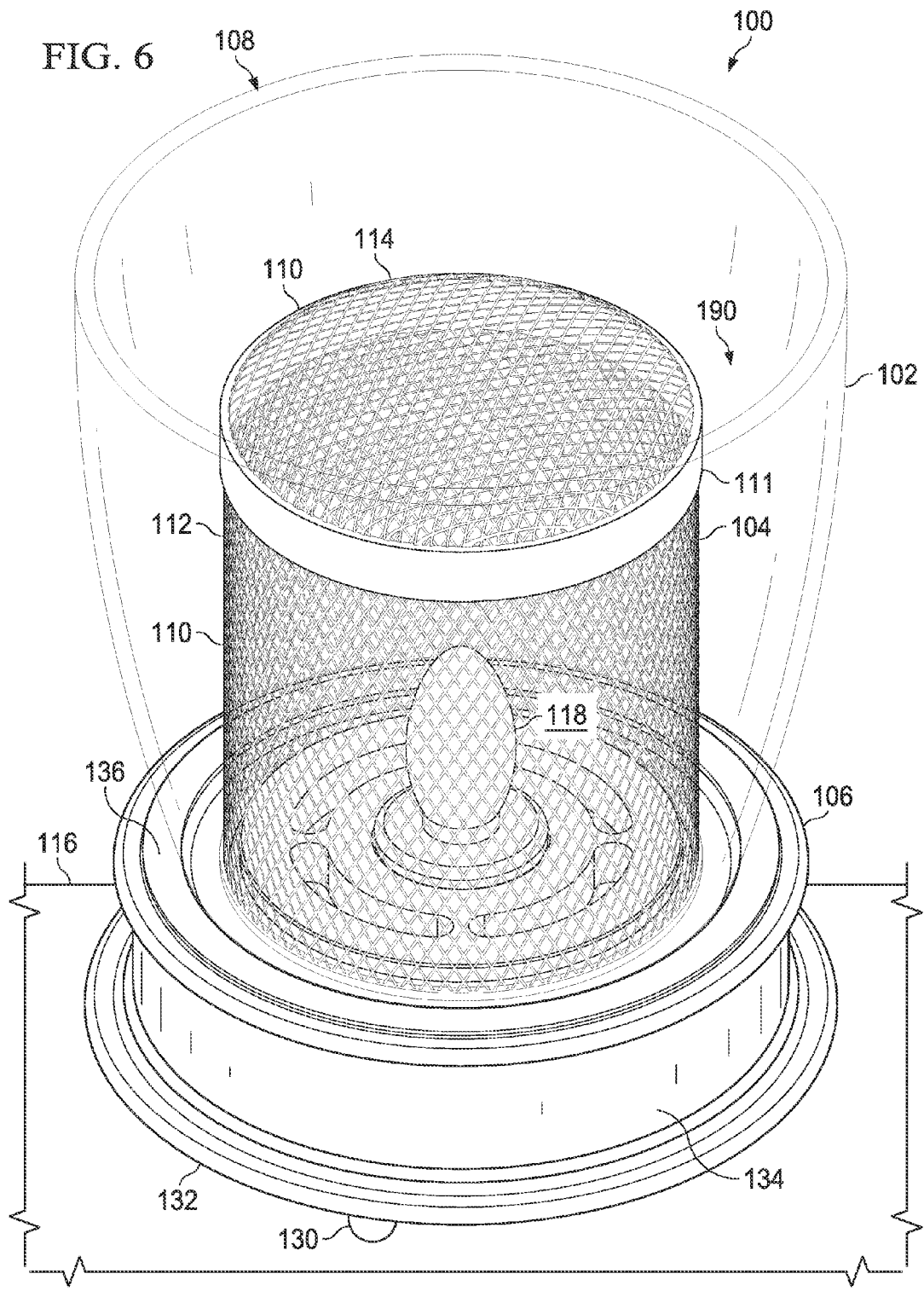
FIG. 6 is a perspective view of another embodiment of a fragrance emitter in accordance with this disclosure.

FIG. 6 is a perspective view of another embodiment of a fragrance emitter 100 that generally includes a shell 102, a barrier 104 and a base 106. The shell 102 includes a fragrance dispensing opening 108 and a second opening 109 (FIG. 7) at the intersection of the shell 102 and the base 106. The shell 102 may be similar to the shell 15 described above and may be any suitable shape, size and material. Furthermore, the fragrance dispensing opening 108 and the second opening 109 may also be any suitable shape and size. In some embodiments, for example, the fragrance dispensing opening 108 is larger than the second opening 109 while in other embodiments the second opening 109 is larger than the fragrance dispensing opening 108. The shell 102 may be any suitable height and may be fluted, concentric, non-concentric or any other shape. The shell 102 may be transparent, translucent, opaque or a combination of transparent, translucent and opaque. The shell 102 may be made of any suitable material and may be, for example, made of a glass material or a ceramic material. The shell 102 may be solid and impermeable to air or may be made of an air permeable material, such as a mesh material, that allows air to pass therethrough.

The shell 102 at least partially surrounds the barrier 104. The barrier 104 may be similar to the permeable screen 31 described above. In the embodiment of FIG. 6, the barrier 104 includes a permeable surface 110 that covers at least a portion of the barrier 104. The barrier 104 also includes an impermeable surface 111 that covers at least a portion of the barrier 104 and couples the permeable surfaces 110 on the upper surface 114 and the lateral surface 112 of the barrier 104. The permeable surfaces 110 of the barrier 104 may be made of any suitable material, such as, for example, a metal mesh material, a glass material or a ceramic material.

In some embodiments, the barrier 104 is any element that provides a barrier between the heating element 118 and the fragrance carriers 150. In some embodiments, the barrier 104 is coupled to the heating element 118 to provide a barrier between the heating element 118 and the fragrance carriers 150. For example, in some embodiments, the heating element 118 is a ceramic heating element and the barrier 104 is a scented sleeve that is coupled to and at least partially encircles the heating element 118. In some embodiments, the sleeve is rubber and at least partially encircles the heating element 118.

The base 106 is positioned below the shell 102 and the barrier 104 to support the shell 102 and the barrier 104. In some embodiments, the shell 102, the barrier 104 and the base 106 are separate pieces that are removably coupled together. In other embodiments, the shell 102, the barrier 104 and the base 106 may be one unitary piece or may be otherwise permanently coupled together. The base 106 includes a plurality of feet 130 that elevate the bottom surface 132 of the base 106 from a surface 116 on which the base 106 is placed. As will be described in more detail below, the feet 130 allow for ambient air to pass between the surface 116 and the base 106 and into the fragrance emitter 100. In other embodiments, the bottom surface 132 of the base 106 contacts the surface 116 and the base 106 has additional openings (not show) in a sidewall 134 or upper wall 136, or both, of the base 106 to allow air to enter the fragrance emitter 100.

Figure 7:
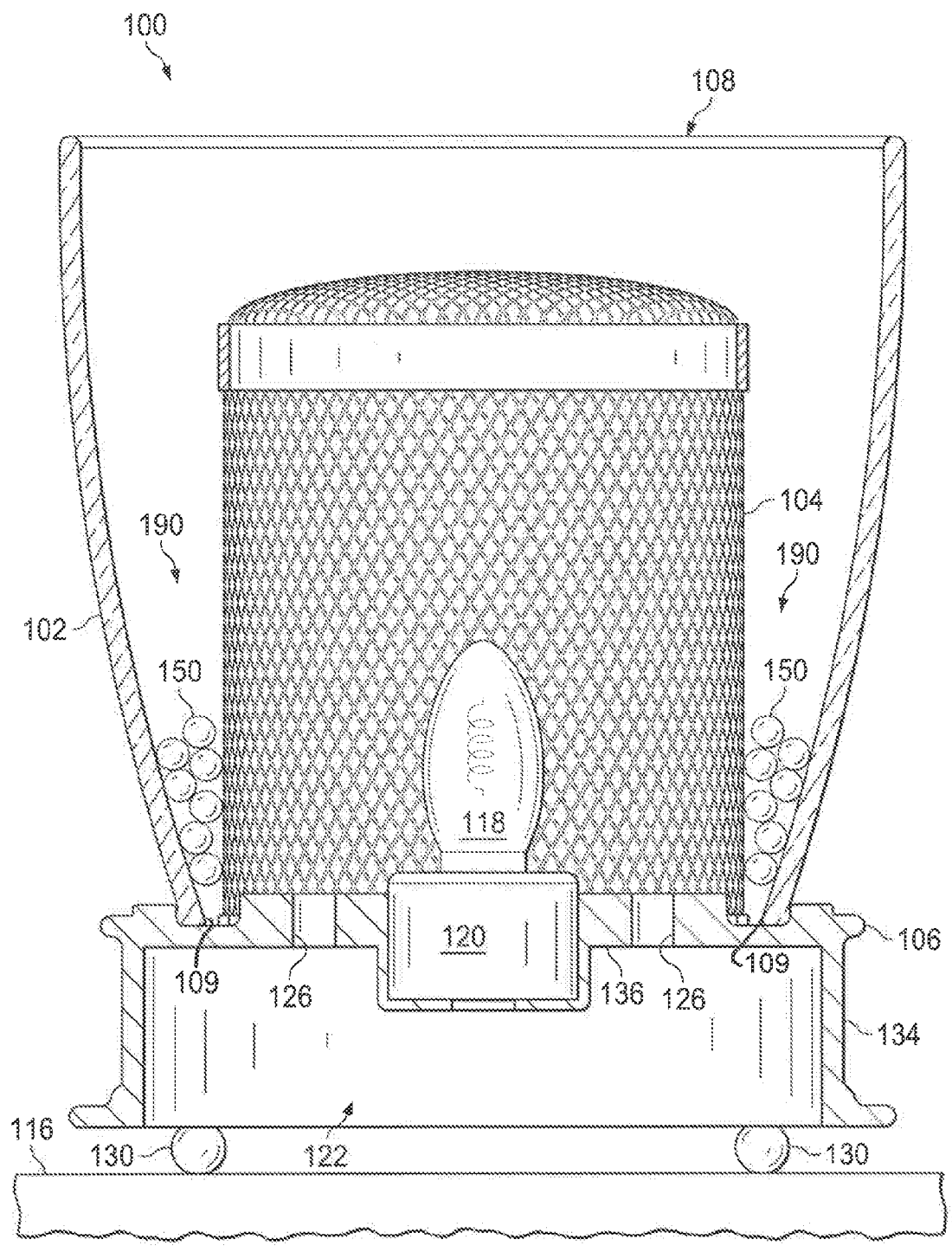
FIG. 7 is a cutaway side view of the fragrance emitter of FIG. 6 cut along a vertical plane.

FIG. 7 is a cutaway side view of the embodiment of a fragrance emitter 100 shown in FIG. 6. As shown in FIG. 7, the modular fragrance emitter 100 includes a heating element 118 which may be similar to the heating element 55. The heating element 118 is located near the base 106 and, in some embodiments, is connected to the base 106. The heating element 118 is coupled to an electronic connection 120 to provide electricity to the heating element 118, if needed. For example, in some embodiments, the heating element 118 is a light bulb and the electronic connection 120 couples the light bulb to an electric cord (not shown).

The base 106 includes an open interior volume 122 between the side wall 134 and upper wall 136 of the base 106. The interior volume 122 is cylindrically shaped in the embodiment shown in FIG. 7, but the interior volume 122 may be any suitable shape in other embodiments.

The base 106 also includes openings 126 extending through an upper wall 136 of the base 106. The openings 126 allow air to flow between the interior volume 122 of the base 106 and an interior volume of the barrier 104. The openings 126 may be any suitable shape and size and the base 106 may include any number of openings 126. In some embodiments, the base 106 includes a plurality of openings 126 that are oriented in a circle around the heating element 118. The openings 126 may be located between the heating element 118 and the barrier 104. In other embodiments, the openings 126 are located between the barrier 104 and the shell 102. In still other embodiments, the base 106 includes openings 126 between the heating element 118 and the barrier 104 and between the barrier 104 and the shell 102. In some embodiments, the base 106 does not include openings 126 and air flow through the fragrance dispensing opening 108 may be sufficient to release fragrance from the fragrance emitter 100.

Figure 8:
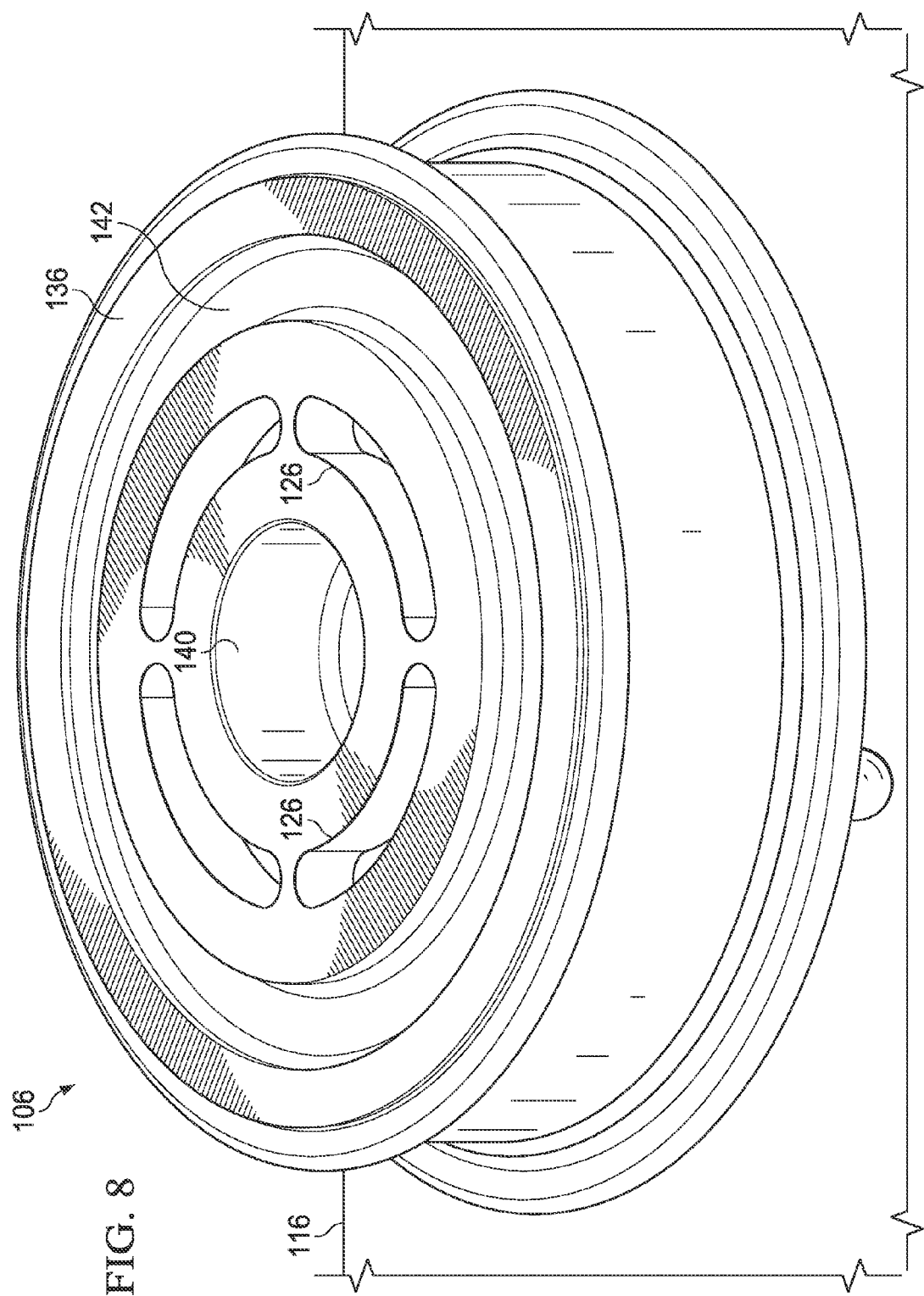
FIG. 8 is a perspective view of one embodiment of a base of a fragrance emitter in accordance with this disclosure.

FIG. 8 is a perspective view of an embodiment of a base 106 of a fragrance emitter 100 that includes openings 126, a central opening 140 to house an electronic connection 120 (FIG. 7) or a heating element 118 (FIG. 7), and a trough 142 to house a portion of the shell 102 and the barrier 104. As described above, the base 106 includes a plurality of openings 126 that are oriented in a circle around the central opening 140. The trough 142 is formed in an upper wall 136 of the base 106 and is configured to hold a lower portion of the shell 102 and the barrier 104. In some embodiments, the trough 142 removably holds the shell 102 in place so that the fragrance dispensing opening 108 of the shell 102 is centrally located above the heating element 118.

Referring again to FIG. 7, the shell 102 and barrier 104 may be made of any suitable material and may be any suitable size. In some embodiments, the shell 102 is made of a material that is impermeable to air, such as glass, while the barrier 104 is made of a material that is permeable to air, such as a metal mesh material. In some embodiments, the shell 102 is made of an air permeable material and the barrier 104 is also made of an air permeable material. In other embodiments, the shell 102 and the barrier 104 are both made of an air impermeable material. In still other embodiments, the shell 102 and the barrier 104 are both made of an air permeable material.

To assemble and operate the modular fragrance emitter 100, a base 106, barrier 104, shell 102 and heating element 118 are selected. As described above, the barrier 104 and/or the shell 102 may form part of the base 106 or may be separate parts that are coupled to the base 106 or rest on the base 106. The heating element 118 is positioned on the base 106, or as shown in FIG. 3, on a base core 51, and is electrically linked to a power source (not shown), if necessary. The barrier 104 is positioned on the base 106 over the heating element 118 and the shell 102 is positioned on the base 106 over the barrier 104. One or more fragrance carriers 150 are then placed in the fragrance carrier cavity 190, for example, by placing the fragrance carriers 150 through the fragrance dispensing opening 108 of the shell 102. As described above, various sizes, shapes and types of bases 106, barriers 104, shells 102 and fragrance carriers 150 may be chosen to customize the modular fragrance emitter 100. To begin emitting fragrance from the modular fragrance emitter 100, the heating element 118 is engaged and heat from the heating element 118 heats the air in the interior volume of the barrier 104 and around the barrier 104. The heat from the heating element 118 may also heat the barrier 104, the shell 102 and/or the fragrance carriers 150. To stop or slow the emission of fragrance, the heating element 118 is disengaged. In some embodiments, the amount of light and/or heat emitted from the heating element 118 is variable and can be automatically or manually varied by a user to adjust the amount of scent released by the modular fragrance emitter 100.

The fragrance carriers 150 may be any suitable type of fragrance emitting element. In some embodiments, the fragrance carriers 150 are solid and do not melt when heated. As such, the fragrance carriers 150 do not liquefy when heated, thus preventing liquid fragrance emitters from being spilled from the fragrance emitter 100 and/or being burnt by the heating element 118. In some embodiments, the fragrance carriers 150 are solid and do not emit soot or smoke when heated. As such, the fragrance emitter 100 does not become dirty from soot or smoke when in use. In some embodiments, the fragrance carriers 150 do not change phase when heated. In some embodiments, the solid fragrance carriers 150 release a vapor fragrance when heated. In some embodiments, the solid fragrance carriers 150 soften slightly when heated. In some embodiments, the fragrance carriers 150 can be used for between about 3 and about 4 weeks.

The fragrance carriers 150 may be any suitable shape and size. For example, in some embodiments the fragrance carriers 150 are spherical beads. In some embodiments, the fragrance carriers 150 are translucent and/or transparent. In some embodiments, the fragrance carriers 150 are colored. In some embodiments, the fragrance carriers 150 are made of one or more of the following materials: wood, plastic, glass, ceramic and metal. In some embodiments, the fragrance carriers 150 are made of a copolymer, one or more process aids and vinyl acetate. In some embodiments, the fragrance carriers 150 include an outer shell made of a different material than the remainder of the fragrance carrier 150.

The fragrance carriers 150 may be made by any suitable process. In some embodiments, solid, spherical beads tumble for about ten minutes at high speed to polish edges of the beads. The beads then move across a vibratory screen to remove dust and small particles from the beads that could become lodged in the barrier 104 or other areas of the emitter 100. The beads are then heated to about 90 degrees Fahrenheit and a mixture of fragrance material and color material is created and mixed together for about 5 minutes. The heated beads and the fragrance/color mixture are then placed in a mixer, such as a ribbon blender, and the blender/mixer mixes the beads and the fragrance/color mixture for about 30 minutes. The blender/mixer stops and the beads rest for about one hour. The blender/mixer then alternates mixing the beads for periods of 5 minutes and resting for periods of 30 minutes until the beads are dry.

In the foregoing description of certain embodiments, specific terminology has been resorted to for the sake of clarity. However, the disclosure is not intended to be limited to the specific terms so selected, and it is to be understood that each specific term includes other technical equivalents which operate in a similar manner to accomplish a similar technical purpose. Terms such as "left" and "right", "front" and "rear", "above" and "below" and the like are used as words of convenience to provide reference points and are not to be construed as limiting terms.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise", "comprised" and "comprises" where they appear.

In addition, the foregoing describes only some embodiments of the invention(s), and alterations, modifications, additions and/or changes can be made thereto without departing from the scope and spirit of the disclosed embodiments, the embodiments being illustrative and not restrictive.

Furthermore, while invention(s) have been described in connection with what are presently considered to be the most practical and preferred embodiments, it is to be understood that the inventions are not to be limited to the disclosed embodiments. Also, the various embodiments described above may be implemented in conjunction with other embodiments, e.g., aspects of one embodiment may be combined with aspects of another embodiment to realize yet other embodiments. Further, each independent feature or component of any given assembly may constitute an additional embodiment.

What is claimed is:

1. A system for producing a fragrance, the system comprising:
   a heating element;
   a barrier at least partially surrounding the heating element;
   a shell at least partially surrounding the barrier to create a volume between the barrier and the shell; and
   a plurality of solid fragrance carriers positioned within at least a portion of the volume between the barrier and the shell, wherein the heating element is configured to generate a thermally induced airflow through the plurality of solid fragrance carriers to emit the fragrance.

2. The system according to claim 1, further comprising a base, the base configured to support the barrier, the shell, and the heating element.

3. The system according to claim 2, wherein the base comprises one or more feet configured to hold at least a portion of the base above a surface on which the feet are resting.

4. The system according to claim 2, further comprising a ventilation channel that extends between an opening in the base and a fragrance dispensing opening in the shell.

5. The system according to claim 4, wherein the opening in the base is positioned at a location between the heating element and the barrier.

6. The system according to claim 4, wherein the opening in the base is positioned at a location between the barrier and the shell.

7. The system according to claim 2, wherein the base comprises of one or more openings positioned to allow ambient air to pass through the base and into an area between the heating element and the barrier.

8. The system according to claim 1, wherein the shell comprises a first opening positioned adjacent to the heating element and an opposite, second opening, wherein the second opening is larger than the first opening.

9. The system according to claim 1, wherein the barrier comprises an air permeable material and the shell comprises an air impermeable material.

10. The system according to claim 1, wherein the thermally induced airflow is generated by heating ambient air using the heating element.

11. An apparatus for producing a fragrance, the apparatus comprising:
   a heating element;
   a first barrier at least partially surrounding the heating element; and
   a second barrier at least partially surrounding the first barrier, the second barrier spaced apart from the first barrier to form a cavity between the first barrier and the second barrier to retain a plurality of solid fragrance carriers positioned within at least a portion of the cavity,
   wherein the heating element is configured to generate a thermally induced airflow through the plurality of solid fragrance carriers to emit the fragrance.

12. The apparatus according to claim 11, wherein the first barrier comprises an air-permeable material.

13. The system according to claim 1, wherein the solid fragrance carriers are configured not to melt when the heating element generates the thermally induced airflow through the plurality of solid fragrance carriers.

14. The system according to claim 1, wherein the barrier and the shell comprise an air permeable material.

15. The apparatus according to claim 11, wherein the thermally induced airflow is generated by heating ambient air using the heating element.

16. The apparatus according to claim 11, wherein the first barrier, the second barrier, and the plurality of solid fragrance carriers are at least partially light permeable.

17. The apparatus according to claim 11, wherein the first barrier comprises a receptacle for a liquid or liquefiable fragrance carrier.

* * * * *